United States Patent [19]

Chibata et al.

[11] 4,381,239

[45] Apr. 26, 1983

[54] METHOD FOR REDUCING THE PYROGEN CONTENT OF OR REMOVING PYROGENS FROM SUBSTANCES CONTAMINATED THEREWITH

[75] Inventors: Ichiro Chibata, Suita; Tetsuya Tosa, Kyoto; Tadashi Sato, Takatsuki; Taizo Watanabe, Nagaokakyo; Satoshi Minobe, Osaka, all of Japan

[73] Assignee: Tanabe Seiyaku Co., Ltd., Osaka, Japan

[21] Appl. No.: 343,269

[22] Filed: Jan. 27, 1982

[30] Foreign Application Priority Data

Feb. 10, 1981 [GB] United Kingdom ................. 8103972

[51] Int. Cl.³ .............................................. B01D 15/00
[52] U.S. Cl. ..................................... 210/679; 210/692
[58] Field of Search ................. 210/660, 679, 690–692, 210/908, 927; 252/426; 424/78–83, 250, 253; 548/344

[56] References Cited

U.S. PATENT DOCUMENTS 3,959,128 5/1976 Harris .................................. 210/692
4,059,512 11/1977 Harris .................................. 210/692
4,168,300 9/1979 Andersson et al. ................. 210/679

*Primary Examiner*—Ivars C. Cintins
*Attorney, Agent, or Firm*—Jordan B. Bierman; Linda Bierman

[57] ABSTRACT

A method for removing a pyrogen from a solution of a pyrogen-containing substance such as an amino acid, a nucleic acid base, an antibiotic, a hormone, a vitamin, an enzyme, an antibody or the like comprising contacting the solution with an adsorbent to adsorb the pyrogen, which is characterized in that the adsorbent comprises a water-insoluble carrier and a nitrogen-containing heterocyclic compound of the formula:

R—A—X wherein R is a nitrogen-containing heterocyclic group; A is single bond, alkylene or alkenylene; X is hydrogen or a functional group; and the heterocyclic group and alkylene may be optionally substituted by one or more substituents, and the compound being bonded to the carrier directly or through a spacer.

15 Claims, No Drawings

METHOD FOR REDUCING THE PYROGEN CONTENT OF OR REMOVING PYROGENS FROM SUBSTANCES CONTAMINATED THEREWITH

The present invention relates to a method for at least reducing pyrogens from various substances contaminated with them.

Pyrogens are pyrogenetic substances which abnormally raise the body temperature of a homothermic animal in a very small amount. When a pyrogen is directly intermixed with blood in the human body, for example, by intravenous injection of a medicine contaminated with it, apart from the main activity of the medicine, the pyrogen causes severe fever. It is said that, when this action of the pyrogen becomes serious, it causes severe fever accompanied with chill and shudder and, occasionally, death from a shock.

Many substances such as bacterial substances, inflammatory substances, vegetable polysaccharides, blood-type substances and the like have been known as pyrogens. Among them, bacterial substances have the most important influence on fever and are called bacterial toxins. Generally, bacterial toxins are classified into exotoxins and endotoxins. Particularly, an endotoxin acting as so called O-antigen, the main component of which is a cell wall-lipopolysaccharide (LPS) of a gram negative bacterium, has the strongest pyrogenicity. Once a substance is contaminated with such the pyrogen, it is very difficult to remove it from the substance.

It has hitherto been known that pyrogens can be removed by various methods, for example, (1) by using charcoal, an ion exchange resin or the like to adsorb a pyrogen, (2) by decomposing a pyrogen with an acid or an alkali, (3) by oxidatively decomposing a pyrogen with an oxidizing agent such as potassium permanganate, aqueous hydrogen peroxide, sodium hypochlorite or the like, (4) by filtering off a pyrogen with an ultramembrane filter, or the like.

However, it is difficult to completely remove a pyrogen in one operation by these conventional methods. Moreover, there are some disadvantages in these conventional methods. For example, a medicament, from which a pyrogen should be removed, is also adsorbed by the above physical method (1) or is also decomposed by the above chemical methods (2) and (3).

Under these circumstances, we have intensively studied and have now found that pyrogens are specifically adsorbed by an adsorbent comprising a nitrogen-containing heterocyclic compound bonded to a water-insoluble carrier directly or through a spacer.

According to the present invention, there is provided a method for at least reducing the pyrogen content of pyrogen-containing solution by contacting the solution with an adsorbent comprising a water-insoluble carrier and a nitrogen-containing heterocyclic compound of the formula:

R—A—X    (I)

wherein R is a nitrogen-containing heterocyclic group; A is single bond, alkylene or alkenylene; X is hydrogen or a functional group such as an amino, carboxyl or hydroxy group; and the heterocyclic group and alkylene may be optionally substituted by one or more substituents, for example carboxyl or hydroxy, and the compound being bonded to the carrier directly or through a spacer i.e. a molecule introduced between the water-insoluble carrier and the nitrogen-containing heterocyclic compound to space or distance the compound from the carrier.

The adsorbent to be used in the present invention can be prepared e.g. by covalently bonding a nitrogen-containing heterocyclic compound (I) to a water-insoluble carrier directly or through a spacer.

Examples of the nitrogen-containing heterocyclic compound of the present invention are that of the formula (I) wherein R is a nitrogen-containing heterocyclic group having for example an imidazole nucleus, pyrazole nucleus, pyrimidine nucleus, pyridazine nucleus, pyrazine nucleus, purine nucleus, acridine nucleus, triazole nucleus, oxadiazole nucleus, tetrazole nucleus, indazole nucleus, benzotriazole nucleus, benzopyridazine nucleus, benzopyrimidine nucleus, benzopyrazine nucleus or naphthyridine nucleus; A is single bond, an alkylene group having 1 to 12 carbon atoms e.g. methylene, ethylene, propylene, butylene, hexylene, octylene, decamethylene or dodecamethylene, or an alkenylene group having 2 to 12 carbon atoms e.g. vinylene, allylene, butenylene, hexenylene or octenylene; and X is for example hydrogen, amino, hydroxy or carboxyl. The nitrogen-containing heterocyclic group of R and an alkylene group of A may be optionally substituted with one or more substituents (e.g., carboxyl, oxo, alkyl, hydroxy, amino, alkoxy). Preferred examples of the nitrogen-containing heterocyclic compound are those of the formula (I) wherein R is a nitrogen-containing heterocyclic group having imidazole nucleus, pyrimidine nucleus, purine nucleus or acridine nucleus, A is single bond, ethylene or ethylene substituted with carboxyl, and X is hydrogen, amino, carboxyl or hydroxyl. Particularly, the preferred compound of the formula (I) is histidine, histamine, urocanic acid, uracil, orotic acid, cytosine, 5-methylcytosine, 2-amino-4,6-dimethylpyrimidine, 2-amino-4-hydroxy-6-methylpyrimidine, adenine or 6,9-diamino-2-ethoxyacridine.

As the water-insoluble carrier, any water-insoluble carrier which can be bonded to the nitrogen-containing heterocyclic compound (I) directly or through a spacer can be used in the present invention. Representative examples of the water-insoluble carrier are those having a hydroxy group, amino group, carboxyl group or a halogen atom. Preferred examples of the water-insoluble carrier having a hydroxy group are a polysaccharide (e.g. cellulose, agarose, cross-linked dextran, etc.), a hydroxyalkylpolystyrene resin (e.g. hydroxyalkylated styrene-divinylbenzene copolymer, etc.), a polyvinylalcohol or the like. Examples of the water-insoluble carrier having an amino group are an aminoalkylpolysaccharide (e.g. aminoalkylcellulose such as aminoethylcellulose or aminohexylcellulose, aminoalkylagarose such as aminohexylagarose, etc.), a p-aminobenzylpolysaccharide (e.g. p-aminobenzylcellulose, p-aminobenzylagarose, etc.), chitosan, an aminoalkylpolystyrene resin (e.g., aminoalkylated styrene-divinylbenzene copolymer), a polyacrylamide, an aminoalkylpolyacrylamide (e.g. aminoethylpolyacrylamide, etc.), and an aminoalkyl-porous glass (e.g. aminopropyl-porous glass, etc.). Examples of the water-insoluble carrier having a carboxyl group are a carboxyalkylpolysaccharide (e.g. carboxyalkylagarose such as carboxyhexylagarose or carboxypentylagarose, carboxyalkylcellulose such as carboxymethylcellulose, carboxyalkyl-crosslinked dextran such as carboxymethyl-crosslinked dextran, etc.), a carboxyalkylpolyacrylamide (e.g. carboxymethylpolyacrylamide, etc.), and a carboxylic acid resin (e.g. acrylic acid-divinylbenzene copolymer, etc.). Examples of the water-insoluble carrier having a halogen atom are a halogenoalkylpolystyrene resin (e.g. chloromethylated styrene-divinylbenzene copolymer, etc.). When a halogenoalkylpolystyrene resin is used, it can be used as it is or it can be converted into a more activated form. For example, a halogenoalkylpolystyrene resin can be converted into a dialkylthioalkylpolystyrene resin having activity higher than that of the halogenoalkylpolystyrene resin by reacting the resin with dialkyl sulfide.

Before bonding the water-insoluble carrier to the nitrogen-containing heterocyclic compound (I), a spacer may be introduced into the carrier or the compound (I). Representative examples of the spacer are the compounds of formulae: $NH_2(CH_2)_nNH_2$, $HOOC(CH_2)_nCOOH$ (or an acid anhydride thereof), $NH_2(CH_2)_nCOOH$, or $NH_2(CH_2)_nOH$ wherein n is an integer of 1 to 12.

The introduction of the spacer into the carrier can be carried out, for example, by a method described in "KOTEIKA KOSO", I. Chibata Editor, pages 11 to 41, Kodan-sha, Tokyo (1975); "JIKKEN TO OYO AFFINITY CHROMATOGRAPHY", I. Chibata et. al., pages 86 to 90, Kodan-sha, Tokyo (1976); "Affinity Chromatography", C. R. Lowe et. al., pages 205 to 245, John Wiley & Sons, London, New York, Sydney, Toronto (1974); or U.S. Pat. No. 4,090,919.

For example, when the spacer is introduced into the carrier having a hydroxy group or the nitrogen-containing heterocyclic compound (I) having a hydroxy group, the carrier or compound is activated e.g. by a cyanogen halide (e.g. cyanogen bromide, etc.), a monoepoxide (e.g. epichlorohydrin, etc.), a bisepoxide (e.g. 1,4-bis(2,3-epoxypropoxy)butane, etc.), a halogenoacetyl halide (e.g. chloroacetyl chloride, etc.) and then, the resulting activated carrier or compound is reacted with the spacer having an amino group or hydroxy group e.g. $NH_2(CH_2)_nNH_2$, $NH_2(CH_2)_nCOOH$, $NH_2(CH_2)_nOH$. When the spacer is introduced into the carrier having an amino group or the nitrogen-containing heterocyclic compound (I) having an amino group, (1) the carrier or compound is activated by reacting with an aliphatic dialdehyde (e.g. glutaraldehyde, etc.) and then, the resulting activated carrier or compound is reacted with the spacer having an amino group e.g. $NH_2(CH_2)_nNH_2$, $NH_2(CH_2)_nCOOH$, or (2) the carrier or compound is reacted with the spacer having carboxyl group e.g. $HOOC(CH_2)_nCOOH$, $NH_2(CH_2)_nCOOH$ to form an acid amide. When the spacer is introduced into the carrier having a carboxyl group or the nitrogen-containing heterocyclic compound (I) having a carboxyl group, the carrier or compound is reacted with the spacer having an amino group e.g. $NH_2(CH_2)_nNH_2$, $NH_2(CH_2)_nCOOH$ to form an acid amide. Further, when the spacer is introduced into the carrier having a halogen atom, the carrier is condensed with the spacer having an amino group, carboxyl group or hydroxy group e.g. $NH_2(CH_2)_nNH_2$, $NH_2(CH_2)_nCOOH$, $NH_2(CH_2)_nOH$.

In order to prepare the adsorbent used in the present invention by using the above carrier and the nitrogen-containing heterocyclic compound, the methods described in the above "KOTEIKA KOSO", pages 11 to 41, "JIKKEN TO OYO AFFINITY CHROMATOGRAPHY", pages 30 to 82 and U.S. Pat. No. 4,090,919 are employed.

For example, when the carrier having a hydroxy group (hereinafter shown as

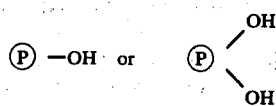

is used, the carrier is activated for example with a cyanogen halide (e.g. cyanogen bromide, etc.), a monoepoxide (e.g. epichlorohydrin, etc.), a bisepoxide (e.g. 1,4-bis(2,3-epoxypropoxy)butane, etc.), halogenoacetyl halide (e.g. chloroacetyl chloride, etc.), and then, the resulting activated carrier is reacted with the nitrogen-containing heterocyclic compound having an amino group (i.e. R—A—NH₂), or the nitrogen-containing heterocyclic compound into which the spacer having an amino group has been introduced (hereinafter, both compounds are shown as Ⓛ—NH₂); or the nitrogen-containing heterocyclic compounds having a hydroxy group (i.e. R—A—OH) or the nitrogen-containing heterocyclic compound into which the spacer having a hydroxy group has been introduced (hereinafter, both compounds are shown as Ⓛ—OH).

According to these processes, the adsorbents of the following formulae can be obtained:

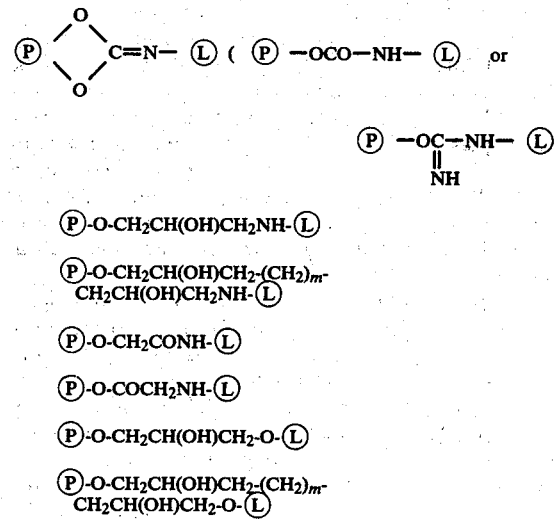

wherein Ⓟ and Ⓛ are as defined above and m is an integer of 1 to 16.

When the water-insoluble carrier having an amino group (hereinafter, shown as Ⓟ-NH₂0 is used, (1) the carrier is activated with an aliphatic dialdehyde (e.g. glutaraldehyde, etc.), the activated carrier is reacted with the nitrogen-containing heterocyclic compound of Ⓛ-NH₂ wherein Ⓛ is as defined above, and then, the resulting Schiff base is reduced with a reducing agent (e.g. sodium borohydride, etc.); (2) the carrier is reacted with the nitrogen-containing heterocyclic compound having a carboxyl group (i.e. R—A—COOH) or the nitrogen-containing heterocyclic compound into which the spacer having a carboxyl group has been introduced (hereinafter, both compounds are shown as Ⓛ-COOH) to form an acid amide; (3) the carrier is activated with a monoepoxide or a bisepoxide and then, the resulting activated carrier is reacted with the nitrogen-containing heterocyclic compound of Ⓛ-NH₂ or Ⓛ-OH; (4) the carrier is activated with cyanuric halide (e.g., cyanuric chloride) and then, the resulting activated carrier is reacted with the nitrogen-containing heterocyclic compound of Ⓛ-NH₂; or (5) the carrier is diazotized and then reacted with the nitrogen-containing heterocyclic compound of Ⓛ-NH₂.

According to these processes, the adsorbents of the following formulae can be obtained:

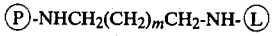

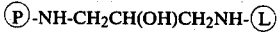

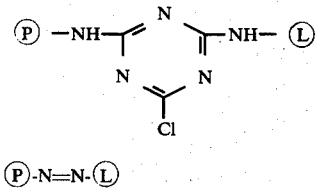

Ⓟ-N=N-Ⓛ wherein Ⓟ, Ⓛ and m are as defined above.

When the water-insoluble carrier having a carboxyl group (hereinafter, shown as Ⓟ-COOH) is used, the carrier is reacted with the nitrogen-containing heterocyclic compound of Ⓛ-NH₂ to form an acid amide.

According to this process, the adsorbent of the formula:

wherein Ⓟ and Ⓛ are as defined above, can be obtained.

Further, when the carrier having a halogen atom (hereinafter, shown as Ⓟ-X, wherein X is halogen) is used, the carrier is reacted with the nitrogen-containing heterocyclic compound of Ⓛ-NH₂, Ⓛ-OH or Ⓛ-COOH.

According to this process, the adsorbent of the following formulae can be obtained:

wherein Ⓟ and Ⓛ are as defined above.

When the nitrogen-containing heterocyclic compound of Ⓛ-NH₂ or Ⓛ-OH is used, the adsorbent used in the present invention can also be obtained by reacting the compound with an epoxy compound and then reacting the resulting activated compound with the carrier of Ⓟ-NH₂ or Ⓟ-OH. Moreover, when uracil is used as the nitrogen-containing heterocyclic compound, the adsorbent can also be obtained by activating the carrier of Ⓟ-NH₂ or Ⓟ-OH with an epoxy compound and then reacting with uracil.

In the adsorbent used in the present invention, the nitrogen-containing heterocyclic compound (I) which is the ligand is preferably bonded in an amount of about 2 to 300 μmol per 1 g (wet form) of the adsorbent.

Since the water-insoluble adsorbent thus obtained specifically adsorbs a pyrogen, a pyrogen-free solution can be obtained from a pyrogen-containing solution by contacting the pyrogen-containing solution with the adsorbent, followed by separating the solution from the adsorbent.

A pyrogen-containing solution to be contacted with the adsorbent preferably has a pH value of 4 to 10 and a specific conductivity of 0 to 10 m mho. When a solution does not have these values then a pretreatment such as for example desalting, dilution or neutralization can be effected to adjust the condition of the solution.

When contacting a pyrogen-containing solution with the adsorbent, either a continuous process using a column or a batch-wise process can be employed, for example.

For example, when a column is used, the adsorbent may be packed in the column and washed with a salt solution, water, a buffer solution and then, a pyrogen-containing solution is passed through the column to adsorb pyrogen on the adsorbent and to obtain a pyrogen-free solution as an effluent. In this case, a pyrogen-containing solution is preferably passed through the column at a flow rate of, generally, 2 to 13 of space velocity (SV). The ratio of a pyrogen-containing solution to the adsorbent is preferably about 5 to 1500 ml of the solution per 1 ml of the adsorbent.

On the other hand, when a batch-wise process is carried out, a pyrogen-containing solution is added to the adsorbent, the resulting mixture is stirred to adsorb pyrogen on the adsorbent and then, the solution is separated from the adsorbent to obtain a pyrogen-free solution. In this case, the ratio of a pyrogen-containing solution to the adsorbent is preferably about 5 to 50 ml of the solution per 1 ml of the adsorbent.

It is preferable to carry out the procedure at 4° to 50° C. in both cases of a continuous process and a batch-wise process.

Since a pyrogen adsorbed on the adsorbent can be removed from the adsorbent by successively washing with aqueous sodium deoxycholate, aqueous sodium hydroxide, aqueous sodium chloride and the like, the adsorbent can be used repeatedly.

The method of the present invention can be employed for reducing the pyrogen content of a pyrogen-containing physiologically active substance, for example an amino acid (e.g. histidine, alanine, proline, etc.), a nucleic acid base (e.g. cytosine, etc.), an antibiotic (e.g. penicillin, etc.), a hormone (e.g. insulin, etc.), a vitamin (e.g. flavin adenine dinucleotide, etc.), a serum protein (e.g. albumin, etc.), an enzyme (e.g. urokinase, asparaginase, lysozyme, etc.), or an antibody (e.g. immunoglobulin, etc.). Moreover, the method of the present invention can be used for producing pyrogen-free water.

The following preparations and examples further illustrate the present invention in detail but are not to be construed to limit the scope thereof.

In the examples, the concentration of pyrogen was measured by the enzymological method using the enzyme in the extract of blood cells of Limulus and the synthetic substrate thereof (J. Med. Enzymol., 3, 43–60 (1978)) and, optionally by the combination of Limulus test and Pyrogen test using rabbits described in Japanese Pharmacopeia IX, P-681.

In the preparations, the content of the nitrogen-containing heterocyclic compound in the adsorbent was calculated from the difference between the result of ninhydrin reaction or UV absorption of the solution containing the compound before the reaction in the preparation and that of the washings after the reaction.

Preparation 1

(1) Sepharose CL-4B (trade name of an agarose derivative manufactured by Pharmacia Fine Chemicals, 30 g, wet form) was thoroughly washed with aqueous 1 M sodium chloride and then water and suspended in water (45 ml). 2 N aqueous sodium hydroxide (19.5 ml) and epichlorohydrin (4.5 ml) were added to the suspension and the mixture was stirred at 40° C. for 2 hours. After completion of the reaction, the mixture was filtered and the residue was washed with water to obtain epoxy-Sepharose CL-4B. Epoxy-Sepharose CL-4B thus obtained was suspended in an 0.625% aqueous solution of hexamethylenediamine (120 ml) and the suspension was stirred at 60° C. for 2 hours. The reaction mixture was filtered and the residue was washed with water to obtain aminohexyl-Sepharose CL-4B (32.8 g, wet form). When the aminohexyl content of the resulting Sepharose was measured by titration, it was about 65 $\mu$mol/g (wet form).

(2) Aminohexyl-Sepharose CL-4B (6 g, wet form) was suspended in 0.05 M phosphate buffer (15.2 ml, pH 7.0). A 25% aqueous solution of glutaraldehyde (6.4 ml) was added to the suspension and the mixture was stirred at room temperature for 2 hours. The reaction mixture was filtered, and the residue was washed with 0.1 M phosphate buffer (pH 7.0) and then suspended in a solution of 15 mM histamine in 0.1 M phosphate buffer (19.5 ml, pH 7.0). The suspension was stirred at room temperature for 2 hours. After completion of the reaction, the mixture was filtered, and the residue was washed with 1 M aqueous sodium chloride (ca. 200 ml) and then suspended in 0.1 M phosphate buffer (10 ml, pH 7.0). Sodium borohydride (100 mg) was added to the suspension and the mixture was stirred at room temperature for 1 hour. The reaction mixture was filtered and the residue was thoroughly washed with 1 M aqueous sodium chloride and water to obtain the water-insoluble adsorbent (6.0 g, wet form) of the formula:

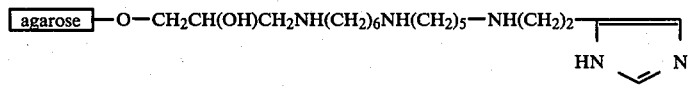

The content of histamine per 1 g (wet form) of the adsorbent thus obtained was 6.5 $\mu$mol.

Preparation 2

(1) Cellulose 90 g (wet form) was suspended in 1 N aqueous sodium hydroxide (900 ml). Epichlorohydrin (100 ml) was added to the suspension and the mixture was stirred at 60° C. for 30 minutes. After completion of the reaction, ice-water was added to the reaction mixture. The mixture was filtered and the residue was washed with water to obtain epoxy-activated cellulose (82 g, wet form). A 0.625% aqueous solution of hexamethylenediamine (400 ml) was added to epoxy-activated cellulose thus obtained (82 g, wet form) and the mixture was stirred at 60° C. for 2 hours. The reaction mixture was filtered and the residue was washed with water to obtain aminohexylcellulose (78 g, wet form). When the aminohexyl content of the resulting cellulose was measured by titration, it was about 69.4 $\mu$mol/g (wet form).

(2) Aminohexylcellulose thus obtained (2 g, wet form) was suspended in 0.05 M phosphate buffer (15.2 ml, pH 7.0) and a 25% aqueous solution of glutaraldehyde (6.4 ml) was added to the suspension and the mixture was stirred at room temperature for 2 hours. After completion of the reaction, the mixture was filtered, and the residue was thoroughly washed with 0.1 M phosphate buffer (pH 7.0) and then suspended in a solution of 10 mM histamine in 0.1 M phosphate buffer (19.5 ml, pH 7.0). The suspension was stirred at room temperature for 2 hours. The reaction mixture was filtered, and the residue was washed with 1 M aqueous sodium chloride (ca. 200 ml) and then suspended in 0.1 M phosphate buffer (10 ml, pH 7.0). Sodium borohydride (100 mg) was added to the suspension and stirred at room temperature for 1 hour. The reaction mixture was filtered and the residue was thoroughly washed with 1 M aqueous sodium chloride and water to obtain water-insoluble adsorbent (2.0 g, wet form) of the formula:

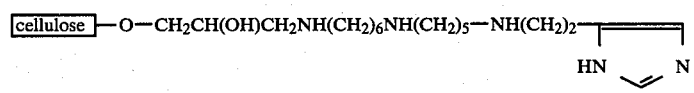

The content of histamine per 1 g (wet form) of the adsorbent thus obtained was 11.2 $\mu$mol.

Preparation 3

The same procedure as described in Preparation 2 was repeated except that histidine was substituted for histamine to obtain the water-insoluble adsorbent (2.0 g, wet form) of the formula:

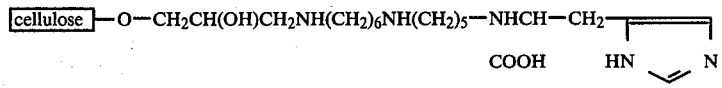

The content of histidine per 1 g (wet form) of the adsorbent was 8.6 $\mu$mol.

Preparation 4

The same procedure as described in Preparation 2 was repeated except that cytosine was substituted for histamine to obtain the water-insoluble adsorbent (2.0 g, wet form) of the formula:

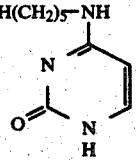

The content of cytosine per 1 g (wet form) of the adsorbent was 8.6 μmol.

Preparation 5

The same procedure as described in Preparation 2 was repeated except that 5-methylcytosine was substituted for histamine to obtain the water-insoluble adsorbent (2.0 g, wet form) of the formula:

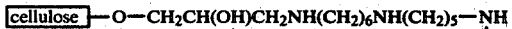

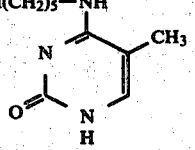

The content of 5-methylcytosine per 1 g (wet form) of the adsorbent was 9.3 μmol.

Preparation 6

The same procedure as described in Preparation 2 was repeated except that 2-amino-4,6-dimethylpyrimidine was substituted for histamine to obtain the water-insoluble adsorbent (2.0 g, wet form) of the formula:

The content of 2-amino-4,6-dimethylpyrimidine per 1 g (wet form) of the adsorbent was 10.0 μmol.

Preparation 7

The same procedure as described in Preparation 2 as repeated except that 2-amino-4-hydroxy-6-methylpyrimidine was substituted for histamine to obtain the water-insoluble adsorbent (2.0 g, wet form) of the formula:

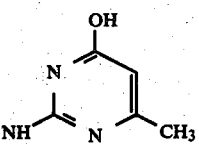

The content of 2-amino-4-hydroxy-6-methylpyrimidine per 1 g (wet form) of the adsorbent was 8.8 μmol.

Preparation 8

The same procedure as described in Preparation 2 was repeated except that adenine was substituted for histamine to obtain the water-insoluble adsorbent (2.0 g, wet form) of the formula:

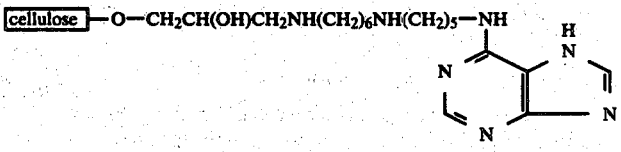

The content of adenine per 1 g (wet form) of the adsorbent was 5.0 μmol.

Preparation 9

The same procedure as described in Preparation 2 was repeated except that 6,9-diamino-2-ethoxyacridine was substituted for histamine to obtain the water-insoluble adsorbent (2.0 g, wet form) of the formula:

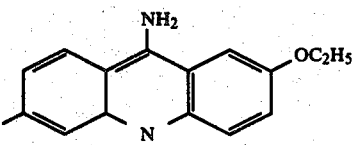

or

-continued

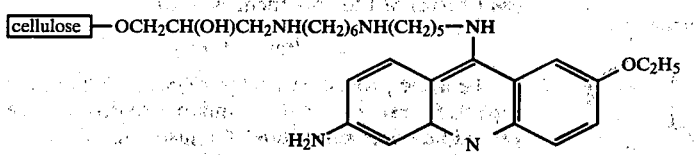

The content of 6,9-diamino-2-ethoxyacridine per 1 g (wet form) of the adsorbent was 6.8 μmol.

Preparation 10

CH-Sepharose 4B (trade name of an agarose derivative manufactured by Pharmacia Fine Chemicals, 6 g, wet form) was suspended in an aqueous solution of 20 mM 5-methylcytosine (9.9 ml) and pH of the suspension was adjusted to 4.5 to 5.0 with 0.5 N hydrochloric acid. A 10% aqueous solution of 1-ethyl-3-(3-dimethylaminopropyl)carbodiimide (1 ml) was added dropwise to the suspension over about 10 minutes while pH of the suspension was maintained at 4.5 to 5.0 by addition of 0.5 N hydrochloric acid. The suspension was stirred at room temperature for 20 hours. The reaction mixture was filtered and the residue was washed with 1 M aqueous sodium chloride (200 ml) to obtain the water-insoluble adsorbent (6.0 g, wet form) of the formula:

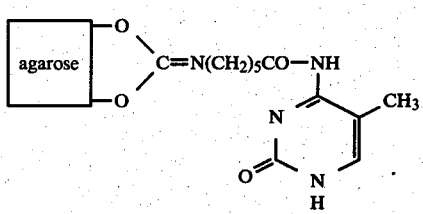

The content of 5-methylcytosine per 1 g (wet form) of the adsorbent was 3.0 μmol.

Preparation 11

1 N aqueous sodium hydroxide (10 ml) and epichlorohydrin (2 ml) were added to hydroxymethylpolystyrene resin (hydroxymethylated styrene-divinylbenzene copolymer, 5 g, wet form) and the mixture was stirred at 60° C. for 1 hour. After completion of the reaction, the mixture was filtered and the residue was washed with water to obtain epoxy-activated hydroxymethylpolystyrene resin. An aqueous solution of 15 mM histamine and 1 M sodium bicarbonate (19.8 ml) was added to the resin and the mixture was stirred at 60° C. for 2 hours. The reaction mixture was filtered and the residue was washed with 1 M aqueous sodium chloride (200 ml) to obtain the water-insoluble adsorbent (5.0 g, wet form) of the formula:

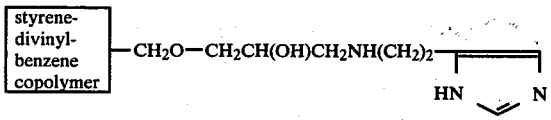

The content of histamine per 1 g (wet form) of the adsorbent was 12.5μ mol.

Preparation 12

Aminopropyl-porous glass (1 g, dry form) was suspended in 0.05 M phosphate buffer (15.2 ml, pH 7.0). A 25% aqueous solution of glutaraldehyde (6.4 ml) was added to the suspension and the mixture was stirred at room temperature for 2 hours. The reaction mixture was filtered, and the residue was thoroughly washed with 0.1 M phosphate buffer (pH 7.0) and then suspended in a solution of 20 mM histamine in 0.1 M phosphate buffer (9.9 ml, pH 7.0). The mixture was stirred at room temperature for 2 hours. The reaction mixture was filtered, the residue was washed with 1 m aqueous sodium chloride and then, reduced with sodium borohydride as described in Preparation 1 to obtain the water-insoluble adsorbent (1.8 g, wet form) of the formula:

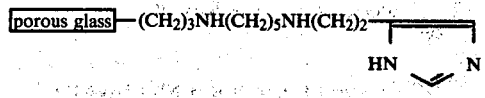

The content of histamine per 1 g (wet form) of the adsorbent was 10.1 μmol.

Preparation 13

Cyanogen bromide-activated Sepharose CL-4B (6 g, wet form) was suspended in an aqueous solution of 20 mM histamine and 1 M sodium bicarbonate (9.9 ml) and the suspension was stirred at room temperature for 20 hours. After completion of the reaction, the mixture was filtered and the residue was washed with 1 M aqueous sodium chloride (200 ml) to obtain the water-insoluble adsorbent (5.9 g, wet form) of the formula:

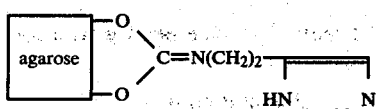

The content of histamine per 1 g (wet form) of the adsorbent was 30.8 μmol.

Preparation 14

Hitamine dihydrochloride (1.84 g) was dissolved in a mixed solution of methanol (30 ml) and 2 N aqueous sodium hydroxide (20 ml) and the chloromethylpolystyrene resin (chloromethylated styrene-divinylbenzene copolymer, 3 g, dry form) was suspended in this solution. The suspension was refluxed at 70° to 80° C. for 4 hours. After completion of the reaction, the mixture was filtered and the residue was thoroughly washed with water to obtain the water-insoluble adsorbent (5.0 g, wet form) of the formula:

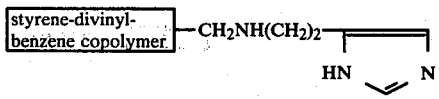

The content of histamine per 1 g (wet form) of the adsorbent was 251 μmol.

Preparation 15

Cellulose (29 g, wet form) was washed with water (1 liter) and suspended in water (150 ml). The suspension was adjusted to pH 11 to 12 by 10 N aqueous sodium hydroxide. A solution of cyanogen bromide (6 g) in water (120 ml) was added to the suspension by portions with stirring while pH of the suspension was maintained at 11 to 12. After completion of the reaction, the mixture was filtered and the residue was washed with cold water (1 liter) and an aqueous ice-cooled solution of 0.1 M sodium bicarbonate to obtain cyanogen bromide-activated cellulose (21 g, wet form). Cyanogen bromide-activated cellulose thus obtained (7 g, wet form) was added to a solution of ethylenediamine (prepared by adjusting an aqueous solution of 50 mM ethylenediamine and 0.1 M sodium bicarbonate (50 ml) to pH 8) and stirred at room temperature for 20 hours. The reaction mixture was filtered and the residue was thoroughly washed with aqueous 1 M sodium chloride and water to obtain aminoethylcellulose (4.5 g, wet form). The same procedure as described in Preparation 2 was repeated except that aminoethylcellulose thus obtained (2 g, wet form) was substituted for aminohexylcellulose to obtain the water-insoluble adsorbent (2.0 g, wet form) of the formula:

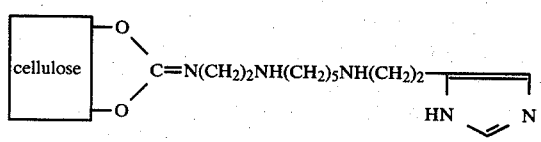

The content of histamine per 1 g (wet form) of the adsorbent was 8.5 μmol.

Preparation 16

Cyanogen bromide-activated cellulose (16.4 g, wet form) obtained in Preparation 15 was added to a solution of butylenediamine (prepared by adjusting an aqueous solution of 40 mM butylenediamine and 0.1 M sodium bicarbonate (50 ml) to pH 10) and the mixture was stirred at room temperature for 20 hours. After completion of the reaction, the mixture was filtered and the residue was thoroughly washed with 1 M aqueous sodium chloride and water to obtain aminobutylcellulose (10.7 g, wet form). The same procedure as described in Preparation 2 was repeated except that aminobutylcellulose thus obtained (2.0 g, wet from) was substituted for aminohexylcellulose to obtain the water-insoluble adsorbent (2.0 g, wet form) of the formula:

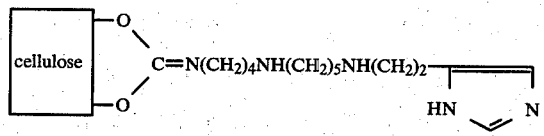

The content of histamine per 1 g (wet form) of the adsorbent was 10.3 μmol.

Preparation 17

Cellulose (177 g, wet form) was suspended in 1 N aqueous sodium hydroxide (1800 ml) at 60° C. Epichlorohydrin (200 ml) was added to the suspension and the suspension was stirred at 60° C. for 30 minutes. Ice-water was added to the reaction mixture. The mixture was filtered and the residue was washed with water to obtain epoxy-activated cellulose (150 g, wet form). An aqueous solution of ethylenediamine (100 ml, containing 5.26 m mol of ethylenediamine and adjusted to pH 11) was added to epoxy-activated cellulose thus obtained (25 g, wet form) and stirred at 60° C. for 2 hours. After completion of the reaction, the mixture was filtered and the residue was thoroughly washed with water to obtain aminoethylcellulose (22 g, wet form). The same procedure as described in Preparation 2 (2) was repeated except that aminoethylcellulose thus obtained (2.0 g, wet form) was substituted for aminohexylcellulose to obtain the water-insoluble adsorbent (2.0 g, wet form) of the formula:

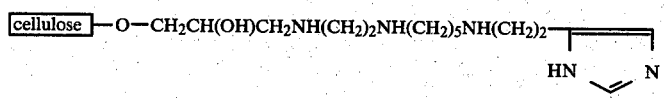

The content of histamine per 1 g (wet form) of the adsorbent was 11.5 μmol.

Preparation 18

The same procedure as described in Preparation 17 was repeated except that butylenediamine was substituted for ethylenediamine to obtain aminobutylcellulose (22 g, wet form). Aminobutylcellulose thus obtained (2 g, wet form) was substituted for aminohexylcellulose in the procedure of Preparation 2 (2) to obtain the water-insoluble adsorbent (2.0 g, wet form) of the formula:

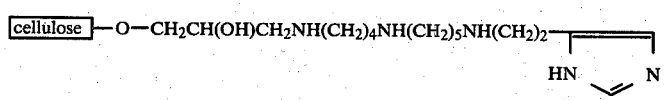

The content of histamine per 1 g (wet form) of the adsorbent was 12.8 μmol.

Preparation 19

The same procedure as described in Preparation 17 was repeated except that hexamethylenediamine was substituted for ethylenediamine to obtain aminohexylcellulose (22 g, wet form). Aminohexylcellulose thus obtained (2 g, wet form) was substituted for aminohexylcellulose in the procedure of Preparation 2 (2) to obtain the water-insoluble adsorbent (2.0 g, wet form) of the formula:

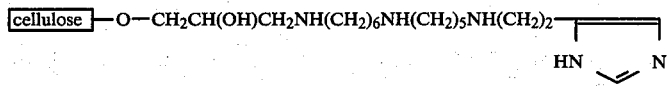

The content of histamine per 1 g (wet form) of the adsorbent was 13.6 μmol.

Preparation 20

The same procedure as described in Preparation 17 was repeated except that octamethylenediamine was substituted for ethylenediamine to obtain aminooctylcellulose (22 g, wet form). Aminooctylcellulose thus obtained (2 g, wet form) was substituted for aminohexylcellulose in the procedure of Preparation 2 (2) to obtain the water-insoluble adsorbent (2.0 g, wet form) of the formula:

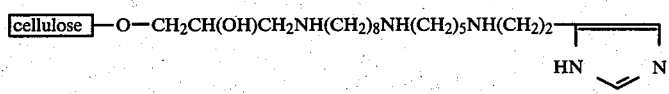

The content of histamine per 1 g (wet form) of the adsorbent was 12.6 μmol.

Preparation 21

A solution of decamethylenediamine (prepared by adjusting a solution of 5.26 m mol of decamethylenediamine in 50% ethanol (100 ml) to pH 11) was added to epoxy-activated cellulose obtained in Preparation 17 (25 g, wet form) and shaken at 60° C. for 2 hours. The reaction mixture was filtered and the residue was thoroughly washed with 50% aqueous ethanol and water to obtain aminodecylcellulose (22 g, wet form). Aminodecylcellulose thus obtained (2 g, wet form) was substituted for aminohexylcellulose in the procedure of Preparation 2 (2) to obtain the water-insoluble adsorbent (2.0 g, wet form) of the formula:

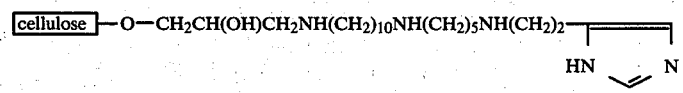

The content of histamine per 1 g (wet form) of the adsorbent was 10.8 μmol.

Preparation 22

The same procedure as described in Preparation 21 was repeated except that dodecamethylenediamine was substituted for decamethylenediamine to obtain aminododecylcellulose (22 g, wet form). Aminododecylcellulose thus obtained (2 g, wet form) was substituted for aminohexylcellulose in the procedure of Preparation 2 (2) to obtain the water-insoluble adsorbent (2.0 g, wet form) of the formula:

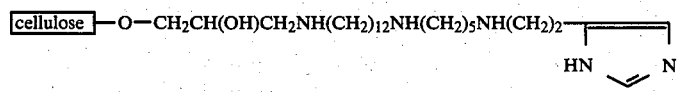

The content of histamine per 1 g (wet form) of the adsorbent was 11.3 μmol.

Preparation 23

Chloromethylpolystyrene resin (chloromethylated styrene-divinylbenzene copolymer, 5 g, dry form) was suspended in a mixed solution of dichloromethane (15 ml) and methanol (15 ml), and triethylamine (1.42 ml) was added to the suspension. The mixture was refluxed at 70° to 80° C. for 4 hours and the resin was filtered off and thoroughly washed with water. Ethylenediamine dihydrochloride (2.66 g) was dissolved in a mixed solvent of methanol (30 ml) and 2 N aqueous sodium hydroxide (20 ml), and the above-obtained resin was suspended in the resulting solution. The suspension was refluxed at 70° to 80° C. for 4 hours. The reaction mixture was filtered and the residue was thoroughly washed with water to obtain a resin (8.4 g, wet form). The resin (5.0 g, wet form) was suspended in 0.05 M phosphate buffer (12 ml, pH 7.0) and a 25% aqueous solution of glutaraldehyde (12 ml) was added to the suspension. The mixture was stirred at room temperature for 2 hours. The reaction mixture was filtered and the residue was thoroughly washed with 0.1 M phosphate buffer (pH 7.0). The residue was suspended in a solution of 15 mM histamine in 0.1 M phosphate buffer (19.5 ml, pH 7.0) and stirred at room temperature for 2 hours. After completion of the reaction, the mixture was filtered, and the residue was washed with 1 m aqueous sodium chloride (ca. 200 ml) and then suspended in 0.1 M phosphate buffer (10 ml, pH 7.0). Sodium borohydride (100 mg) was added to the suspension. The mixture was stirred at room temperature for 1 hour. The reaction mixture was filtered and the residue was thoroughly washed with aqueous 1 M sodium chloride and water to obtain the water-insoluble adsorbent (5.0 g, wet form) of the formula:

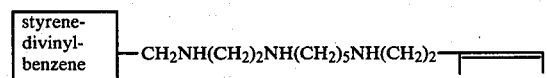

The content of histamine per 1 g (wet form) of the adsorbent was 28.6 μmol.

Preparation 24

The same procedure as described in Preparation 23 was repeated except that hexamethylenediamine (2.32 g) was substituted for ethylenediamine dihydrochloride to obtain the water-insoluble adsorbent (5.0 g, wet form) of the formula:

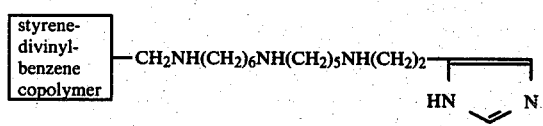

The content of histamine per 1 g (wet form) of the adsorbent was 58.8 μmol.

Preparation 25

(1) N-t-Butoxycarbonyl-ε-aminocaproic acid (2.31 g), 1-hydroxybenzotriazole (1.49 g) and dicyclohexylcarbodiimide (2.27 g) were dissolved in tetrahydrofuran (10 ml). Histamine dihydrochloride (1.84 g) and triethylamine (2.84 ml) were added to the solution and the mixture was stirred at room temperature for 5 hours. After completion of the reaction, the precipitate formed was filtered off and the filtrate was extracted with ethyl acetate. The extract was washed with 1% hydrochloric acid and then saturated aqueous sodium bicarbonate, dried and the solvent was distilled off to obtain N-t-butoxycarbonyl-ε-aminocaproyl histamine as an oil. The oil showed single spot (Rf: 0.76) in thin layer chromatography (solvent: chloroform-methanol-acetic acid (95:5:3). The oil thus obtained was treated with trifluoroacetic acid (5 ml) at room temperature for 30 minutes and ether was added to the mixture to obtain ε-aminocaproyl histamine (1.12 g) as an oil. The oil showed single spot (Rf: 0.47) in thin layer chromatography (solvent: n-butanol-acetic acid-water (4:1:1).

(2) Chloromethylpolystyrene resin (chloromethylated styrene-divinylbenzene copolymer, 5 g, dry form) was suspended in a mixed solution of dichloromethane (15 ml) and methanol (15 ml). Triethylamine (1.42 ml) was added to the suspension and are mixture was refluxed at 70° to 80° C. for 4 hours. The resin was filtered and thoroughly washed with water. ε-Aminocaproyl caproyl histamine obtained in the above (1) (1.12 g) was dissolved in a mixed solution of methanol (30 ml) and 2 N aqueous sodium hydroxide (20 ml) and the above-obtained resin was suspended in this solution. The mixture was reacted at 45° C. to 50° C. for 24 hours. After completion of the reaction, the mixture was filtered and the residue was thoroughly washed with water to obtain the water-insoluble adsorbent (8.4 g, wet form) of the formula:

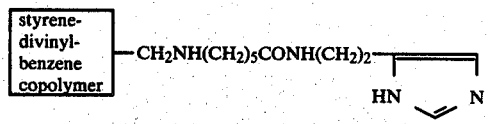

The content of histamine per 1 g (wet form) of the adsorbent was 59.5 μmol.

Preparation 26

Aminohexyl-Sepharose CL-4B (6 g, wet form, prepared in Preparation 1 (1)) was suspended in an aqueous solution of 30 mM urocanic acid (9.9 ml). The suspension was adjusted to pH 4.5 to 5.0 with 0.5 N hydrochloric acid and 40% aqueous solution of 1-ethyl-3-(3-dimethylaminopropyl)carbodiimide (1 ml) was added dropwise to the suspension over 10 minutes, while the suspension was maintained at pH 4.5 to 5.0 by addition of 0.5 N hydrochloric acid. After addition, the reaction mixture was stirred at room temperature for 20 hours. The reaction mixture was filtered and the residue was washed with 1 M aqueous sodium chloride (ca. 200 ml) to obtain the water-insoluble adsorbent (6.0 g, wet form) of the formula:

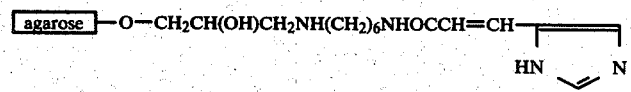

The content of urocanic acid per 1 g (wet form) of the adsorbent was 3.1 μmol.

Preparation 27

The same procedure as described in Preparation 26 was repeated except that an aqueous solution of 10 mM orotic acid (19.9 ml) was substituted for 30 mM aqueous urocanic acid solution (9.9 ml) to obtain the water-insoluble adsorbent (6.0 g, wet form) of the formula:

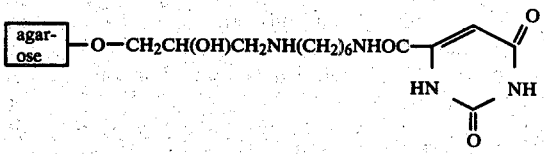

The content of orotic acid per 1 g (wet form) of the adsorbent was 15.3 μmol.

Preparation 28

Aminohexyl-Sepharose CL-4B (6 g, wet form, prepared in Preparation 1 (1)) was suspended in water (9 ml). 2 N aqueous sodium hydroxide (3.9 ml) and epichlorohydrin (0.9 ml) was added to the suspension and the mixture was stirred at 40° C. for 2 hours. The reaction mixture was filtered and the residue was washed with water to obtain epoxy-activated aminohexyl-Sepharose CL-4B. Epoxy-activated aminohexyl-Sepharose CL-4B thus obtained was suspended in an aqueous solution of 30 mM uracil (9.9 ml, adjusted to pH 12 with 2 N sodium hydroxide) and the suspension was stirred at 60° C. for 2 hours. After completion of the reaction, the mixture was filtered and the residue was washed with 1 M aqueous sodium chloride (200 ml) to obtain the water-insoluble adsorbent (6.0 g, wet form) of the formula:

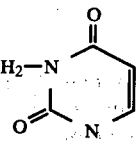

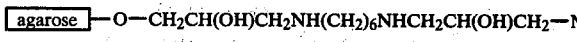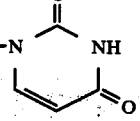

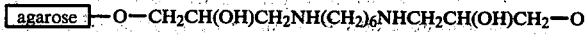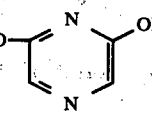

or

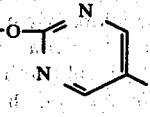

The content of uracil per 1 g (wet form) of the adsorbent was 4.1 μmol.

Preparation 29

(1) Dimethyl sulfide (20 g) was dissolved in a mixed solution of dichloromethane (60 ml), methanol (60 ml) and distilled water (90 ml) and porous chloromethylpolystyrene resin (chloromethylated styrene-divinylbenzene copolymer, 20 g, dry form) was suspended in the solution. The suspension was refluxed at 60° C. for 48 hours. After completion of the reaction, the mixture was filtered and the residue was thoroughly washed with water and methanol to obtain dimethylthiomethyl-polystyrene resin (33 g, wet form).

(2) Histamine dihydrochloride (1.84 g) was dissolved in a mixed solution of 2 N aqueous sodium hydroxide (20 ml) and methanol (10 ml) and dimethylthiomethyl-polystyrene resin obtained in the above (1) (5 g, wet form) was suspended in this solution. The mixture was refluxed at 80° to 85° C. for 21 hours. The reaction mixture was filtered and the residue was thoroughly washed with water to obtain the water-insoluble adsorbent (5.0 g, wet form) of the formula:

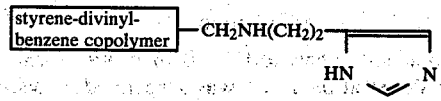

The content of histamine per 1 g (wet form) of the adsorbent was 179 μmol.

Preparation 30

The aminoethylated polystyrene resin (5.0 g, wet form) obtained in the same manner as described in Preparation 23 was suspended in an aqueous 30 mM urocanic acid solution (9.9 ml), and the pH of the suspension was adjusted to 4.5–5.0 with 0.5 N hydrochloric acid. A 40% aqueous solution of 1-ethyl-3-(3-dimethylaminopropyl)carbodiimide (1 ml) was added dropwise to the suspension over about 10 minutes while the pH of the suspension was maintained at 4.5 to 5.0 by addition of 0.5 N hydrochloric acid. The suspension was stirred at room temperature for 20 hours. The reaction mixture was filtered, and the residue was washed with 1 M aqueous sodium chloride (200 ml) to obtain the water-insoluble adsorbent (5.0 g, wet form) of the formula:

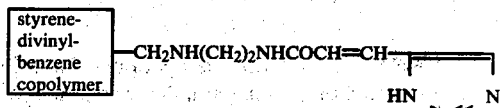

The content of urocanic acid per 1 g (wet form) of the adsorbent was 44.3 μmol.

Preparation 31

The same procedure as described in Preparation 30 was repeated except that an aqueous 10 mM orotic acid solution (19.9 ml) was substituted for the aqueous 30 mM urocanic acid solution (9.9 ml) to obtain the water-insoluble adsorbent (5.0 g, wet form) of the formula:

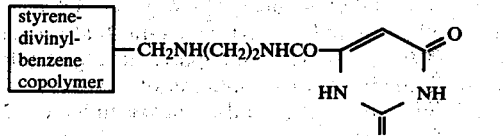

The content of orotic acid per 1 g (wet form) of the adsorbent was 27 μmol.

Preparation 32

The same procedure as described in Preparation 30 was repeated except that the aminohexylated polystyrene resin (5.0 g, wet form) obtained in the same manner as described in Preparation 24 was substituted for the aminoethylated polystyrene resin to obtain the water-insoluble adsorbent (5.0 g, wet form) of the formula:

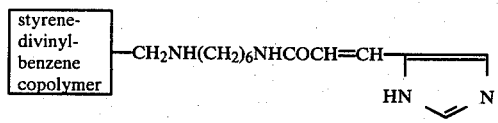

The content of urocanic acid per 1 g (wet form) of the adsorbent was 33 μmol.

Preparation 33

The same procedure as described in Preparation 31 was repeated except that the aminohexylated polystyrene resin (5.0 g, wet form) obtained in the same manner as described in Preparation 24 was substituted for the aminoethylated polystyrene resin to obtain the water-insoluble adsorbent (5.0 g, wet form) of the formula:

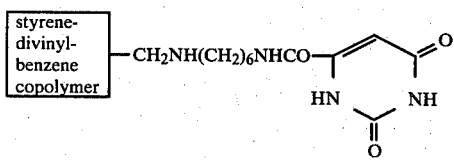

The content of orotic acid per 1 g (wet form) of the adsorbent was 17.2 μmol.

Preparation 34

The same procedure as described in Preparation 23 was repeated except that 5-methylcytosine was substituted for histamine to obtain the water-insoluble adsorbent (5.0 g, wet form) of the formula:

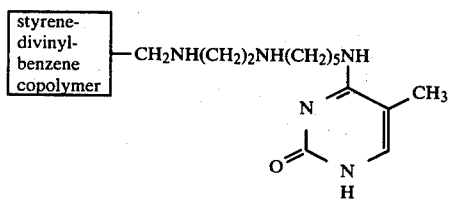

The content of 5-methylcytosine per 1 g (wet form) of the adsorbent was 1.7 μmol.

Preparation 35

Chloromethylpolystyrene resin (chloromethylated styrene-divinylbenzene copolymer) was treated in the same manner as described in J. Am. Chem. Soc., 98, 7357 (1976) to obtain aminomethylated polystyrene resin. The aminomethylated polystyrene resin (5.0 g, dry form) thus obtain was suspended in an aqueous 0.1 M sodium tetraborate solution (40 ml), and cyanuric chloride (3.69 g) was added thereto. The mixture was stirred at room temperature for 2 hours. The reaction mixture was filtered, and the residue was washed with methanol and water to obtain a resin (13.2 g, wet form). An aqueous 25 mM histamine-0.1 M sodium tetraborate solution (19.9 ml) was added to the resin (6.6 g, wet form) obtained above, and the mixture was stirred at room temperature for 2 hours. The reaction mixture was filtered, and the residue was washed with 1 M sodium chloride (200 ml) to obtain the water-insoluble adsorbent (6.6 g, wet form) of the formula:

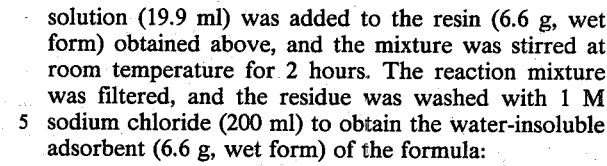

The content of histamine per 1 g (wet form) of the adsorbent was 64.4 μmol.

Preparation 36

The resin (6.6 g, wet form) obtained by reacting the aminomethylated polystyrene resin with cyanuric chloride in the same manner as described in Preparation 35 was added to an aqueous 500 mM ε-aminocaproic acid-0.1 M sodium tetraborate solution (20.3 ml). The mixture was stirred at room temperature for 2 hours. The reaction mixture was filtered, and the residue was washed with an aqueous 1 M sodium chloride solution (200 ml) to obtain a resin (6.6 g, wet form). The resin thus obtained was suspended in an aqueous 30 mM histamine solution (9.9 ml), and the suspension was treated in the same manner as described in Preparation 30 to obtain the water-insoluble adsorbent (6.6 g, wet form) of the formula:

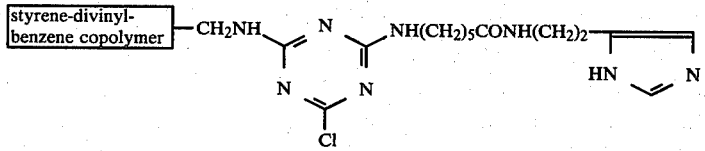

The content of histamine per 1 g (wet form) of the adsorbent was 5.3 μmol.

Preparation 37

(1) An aqueous 3 N sodium hydroxide solution (10 ml) and epichlorohydrin (10 ml) were added to Toyopearl HW-55 (tradename of an polyvinyl alcohol manufactured by Toyo Soda Manufacturing Co., Ltd.) (13 g, wet form). The mixture was shaken at 50° C. for 2 hours. The reaction mixture was filtered, and the residue was washed with water to obtain epoxy-Toyopearl HW-55 (13.7 g, wet form). Epoxy-Toyopearl HW-55 (13.7 g, wet form) was suspended in an aqueous conc. ammonia solution (20 ml), and the suspension was shaken at 50° C. for one hour. The reaction mixture was filtered, and the residue was washed with water to obtain aminopropylated Toyopearl HW-55 (14.3 g, wet form). The content of aminopropyl group per 1 g (wet form) of the aminopropylated Toyopearl HW-55 was about 125 μmol.

(2) Aminopropylated Toyopearl HW-55 (6 g, wet form) was suspended in a 0.05 M phosphate buffer solution (pH 7.0, 12 ml), and an aqueous 25% glutaraldehyde solution (12 ml) was added thereto. The suspension was stirred at room temperature for 30 minutes. The reaction mixture was filtered, and the residue was washed with a 0.1 M phosphate buffer solution (pH 7.0). The residue was suspended in a 15 mM histamine-0.1 M phosphate buffer solution (pH 7.0, 19.8 ml), and the suspension was stirred at room temperature for 2 hours. The reaction mixture was filtered, and the residue was washed with an aqueous 1 M sodium chloride solution (about 200 ml). The residue was suspended in a 0.1 M phosphate buffer solution (pH 7.0, 10 ml), and sodium borohydride (100 mg) was added thereto. The suspension was stirred at room temperature for one hour. The reaction mixture was filtered, and the residue was washed with an aqueous 1 M sodium chloride solution and water to obtain the water-insoluble adsorbent (6.0 g, wet form) of the formula:

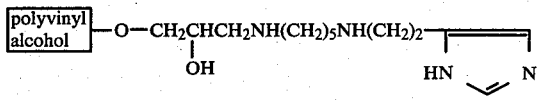

The content of histamine per 1 g (wet form) of the adsorbent was 18.2 μmol.

Preparation 38

(1) Epoxy-Toyopearl HW-55 (9.0 g, wet form) obtained in the same manner as described in Preparation 37 (1) was suspended in an aqueous 0.625% hexamethylenediamine solution (36 ml), and the suspension was shaken at 60° C. for 2 hours. The reaction mixture was filtered, and the residue was washed with water to obtain aminohexyl-Toyopearl HW-55 (8.5 g, wet form). The content of aminohexyl group per 1 g (wet form) of the aminohexyl-Toyopearl HW-55 was about 174 μmol.

(2) The same procedure as described in Preparation 37 (2) was repeated except that aminohexyl-Toyopearl HW-55 was substituted for aminopropyl-Toyopearl HW-55 to obtain the water-insoluble adsorbent (6.0 g, wet form) of the formula:

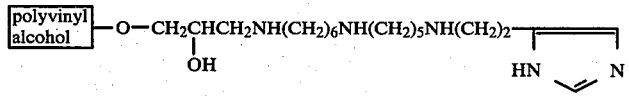

The content of histamine per 1 g (wet form) of the adsorbent was 21.8 μmol.

Preparation 39

(1) Chitosan (5 g, dry form) was dissolved at 50° C. in 0.1 N hydrochloric acid (350 ml), and conc. hydrochloric acid was added to the solution. The precipitates were collected by filtration, and then dispersed in an aqueous 6 N sodium hydroxide solution (200 ml). Methanol (300 ml) was added to the dispersion, and the precipitates were collected by filtration. The precipitates thus obtained were washed with methanol, dried and then passed through a sieve (20 mesh) to obtain mercerized chitosan (3.44 g, dry form).

(2) The same procedure as described in Preparation 37 was repeated except that the mercerized chitosan was substituted for Toyopearl HW-55 to obtain the water-insoluble adsorbent (3.3 g, wet form) of the formula:

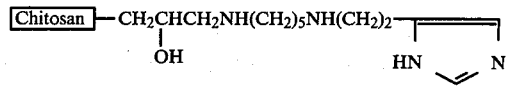

The content of histamine per 1 g (wet form) of the adsorbent was 59.7 μmol.

EXAMPLE 1

The adsorbent obtained in Preparation 1 (ligand: histamine, carrier: aminohexylagarose, 8 ml) was washed with 1.5 M aqueous sodium chloride and packed in a sterilized column (inner diameter: 13 mm, length: 100 mm). The column was successively washed with 1.5 M aqueous sodium chloride (250 ml), pure water (100 ml) and 0.05 M aqueous sodium chloride (100 ml), all of which being pyrogen-free. A solution of each pyrogen (100 μg) derived from various kinds of bacteria in 0.05 M aqueous sodium chloride (100 ml) was passed through the column at a flow rate of SV=12. In this case, only one column was used and the used column was reused by successively washing with 0.2 N aqueous sodium hydroxide (16 ml), 0.5% aqueous solution of sodium deoxycholate (32 ml), 0.2 N aqueous sodium hydroxide (160 ml), pure water (50 ml), 1.5 M aqueous sodium chloride (250 ml) and pure water (100 ml) to reproduce pyrogen adsorptivity of the adsorbent. The concentration of the pyrogen in the effluent was measured and Limulus test thereof was carried out.

The results are shown in Table 1. In Table 1, as the pyrogen derived from Klebsiella pneumoniae, LPS prepared according to Westphal method (Angwt, Chem., 66, 407, (1954)) was used and the other pyrogens were LPS manufactured by Difco Lab, USA.

TABLE 1

| Pyrogens derived from bacteria | Concentration of pyrogen (ng/ml effluent) | Limulus test |
|---|---|---|
| Escherichia coli 0128: B12, LPS | 0.2 | — |
| Klebsiella pneumoniae, LPS | 0 | — |
| Salmonella abortus equi, LPS | 0.6 | — |
| Salmonella enteritidis, LPS | 0.6 | — |
| Salmonella flexineri, LPS | 0 | — |
| Salmonella minnesota 9700, LPS | 0.1 | — |

EXAMPLE 2

Each adsorbent obtained in Preparations 2 to 9 (8 ml) was packed in a column (inner diameter: 13 mm, length: 100 mm) and the column was washed by the same manner as described in Example 1. A solution of a pyrogen in 0.05 M aqueous sodium chloride (100 ml, containing 1,000 ng of Escherichia coli 0128: B 12, LPS per 1 ml of the solution) was passed through the column at a flow rate of SV=12. The concentration of the pyrogen in the effluent was measured. The results are shown in Table 2.

TABLE 2

| No. | Adsorbents | Concentration of pyrogen (ng/ml effluent) |
|---|---|---|
| 1 | Adsorbent of Preparation 2 (ligand: histamine, carrier: aminohexyl-cellulose) | 0.1 |
| 2 | Adsorbent of Preparation 3 (ligand: histidine, carrier: aminohexyl-cellulose) | 0.1 |
| 3 | Adsorbent of Preparation 4 (ligand: cytosine, carrier: aminohexyl-cellulose) | 0.5 |
| 4 | Adsorbent of Preparation 5 (ligand: 5-methylcytosine, carrier: amino-hexylcellulose) | 0.6 |
| 5 | Adsorbent of Preparation 6 (ligand: 2-amino-4,6-dimethylpyrimidine, carrier: aminohexylcellulose) | 0.5 |
| 6 | Adsorbent of Preparation 7 (ligand: 2-amino-4-hydroxy-6-methyl-pyrimidine, carrier: amino-hexylcellulose) | 0.9 |
| 7 | Adsorbent of Preparation 8 (ligand: adenine, carrier: aminohexyl-cellulose) | 4.0 |
| 8 | Adsorbent of Preparation 9 (ligand: acrinol, carrier: aminohexyl-cellulose) | 1.6 |

EXAMPLE 3

The adsorbent obtained in Preparation 10 (ligand: 5-methylcytosine, carrier: carboxyhexylagarose, 8 ml) was packed in a column (inner diameter: 13 mm, length: 100 mm) and the column was washed in the same manner as described in Example 1. When a solution of a pyrogen in 0.05 M aqueous sodium chloride (100 ml, containing 1,000 ng of $Escherichia\ coli$ 0128: B 12, LPS per 1 ml of the solution) was passed through the column at a flow rate of $SV=12$, the concentration of the pyrogen in the effluent was 1.2 ng/ml.

EXAMPLE 4

The adsorbent obtained in Preparation 11 (ligand: histamine, carrier: hydroxymethylated styrenedivinylbenzene copolymer, 8 ml) was packed in a column (inner diameter; 13 mm, length: 100 mm) and the column was washed in the same manner as described in Example 1. When a solution of a pyrogen in 0.05 M aqueous sodium chloride (100 ml, containing 100 ng of $Escherichia\ coli$ 0128: B 12, LPS per 1 ml of the solution) was passed through the column at a flow rate of $SV=12$, the concentration of the pyrogen in the effluent was 4.8 ng/ml.

EXAMPLE 5

The adsorbent obtained in Preparation 12 (ligand: histamine, carrier: porous glass, 1 g, dry form) was suspended in a solution of a pyrogen in 0.05 M aqueous sodium chloride (50 ml, containing 100 ng of $Klebsiella\ pneumoniae$, LPS per 1 ml of the solution). When the suspension was stirred for 2 hours and allowed to stand, the concentration of the pyrogen in the supernatant was 2 ng/ml.

EXAMPLE 6

The adsorbent obtained in Preparation 13 (ligand: histamine, carrier: agarose, 8 ml) was packed in a column (inner diameter: 13 mm, length: 100 mm) and the column was washed in the same manner as described in Example 1. When a solution of a pyrogen in 0.05 M aqueous sodium chloride (100 ml, containing 100 ng of $Escherichia\ coli$ 0128: B 12, LPS per 1 ml of the solution) was passed through the column at a flow rate of $SV=12$, the concentration of the pyrogen in the effluent was 9 ng/ml.

EXAMPLE 7

The adsorbent obtained in Preparation 14 (ligand: histamine, carrier: styrene-divinylbenzene copolymer, 8 ml) was packed in a column (inner diameter: 13 mm, length: 100 mm) and the column was washed in the same manner as described in Example 1. When a solution of a pyrogen in 0.05 M aqueous sodium chloride (100 ml, containing 100 ng of $Salmonella\ flexineri$, LPS per 1 ml of the solution) was passed through the column at a flow rate of $SV=12$, the concentration of the pyrogen in the effluent was 4.6 ng/ml.

EXAMPLE 8

The column used in Example 1 (packed with the adsorbent, the ligand thereof being histamine and the carrier being aminohexylagarose) was successively washed with 0.2 N aqueous sodium hydroxide (16 ml), 0.5% aqueous solution of sodium deoxycholate (32 ml), 0.2 N aqueous sodium hydroxide (160 ml), pure water (50 ml), 1.5 M aqueous sodium chloride (250 ml) and pure water (100 ml), all of which being pyrogen free. A 2% aqueous solution of L-histidine (100 ml, containing 100 ng of $Escherichia\ coli$ 0128: B 12, LPS per 1 ml of the solution) was passed through the column at a flow rate of $SV=3$. In the effluent, more than 90% of L-histidine was recovered and Limulus test of the effluent was negative (−). When the effluent was subjected to Pyrogen test at a dose of 10 ml/kg, the body temperatures of the rabbits rose 0° C., 0.1° C. and 0.25° C., respectively and pyrogenicity of the effluent was deemed to be negative. Besides, when the aqueous solution of L-histidine was directly diluted 5 times with water without subjecting to the treatment of the column and then was subjected to Pyrogen test at a dose of 1 ml/kg, the body temperatures of the rabbits rose 1.15° C., 1.15° C. and 1.30° C., respectively, and pyrogenicity of the solution was deemed to be positive.

EXAMPLE 9

The column used in Example 1 was washed in the same manner as described in Example 8. A 2% aqueous solution of L-alanine (100 ml, containing 100 ng of $Escherichia\ coli$ 0128: B 12, LPS per 1 ml of the solution) was passed through the column at a flow rate of $SV=3$. More than 90% of L-alanine was recovered in the effluent and the concentration of the pyrogen in the effluent was 0.1 ng/ml. Limulus test of the effluent was negative (−).

EXAMPLE 10

The column used in Example 1 was washed in the same manner as described in Example 8. An aqueous solution containing 0.08% of 6-aminopenicillanic acid and 0.08% of sodium citrate (100 ml, containing 100 ng of $Escherichia\ coli$ 0128: B 12, LPS per 1 ml of the solution) was passed through the column at a flow rate of $SV=3$. More than 90% of 6-aminopenicillanic acid was recovered in the effluent and Limulus test of the effluent was negative (−).

EXAMPLE 11

The column used in Example 1 was washed in the same manner as described in Example 8. A 0.25% aqueous solution of flavin adenine dinucleotide (FAD) (100 ml, containing 100 ng of Escherichia coli 0128: B 12, LPS per 1 ml of the solution) was passed through the column at a flow rate of SV=3. More than 85% of FAD was recovered in the effluent and Limulus test of the effluent was negative (−).

EXAMPLE 12

The column used in Example 1 was washed in the same manner as described in Example 8. A 0.5% aqueous solution of cytosine (100 ml, containing 100 ng of Escherichia coli 0128: B 12, LPS per 1 ml of the solution) was passed through the column at a flow rate of SV=3. More than 95% of cytosine was recovered in the effluent and the concentration of the pyrogen in the effluent was 0 ng/ml. Limulus test of the effluent was negative (−).

EXAMPLE 13

The column used in Example 1 was washed in the same manner as described in Example 8. A 5% aqueous solution of glucose (100 ml, containing 100 ng of Escherichia coli 0128: B 12, LPS per 1 ml of the solution) was passed through the column at a flow rate of SV=3. More than 90% of glucose was recovered in the effluent and Limulus test of the effluent was negative (−).

EXAMPLE 14

The column used in Example 1 was washed in the same manner as described in Example 8. A crude L-proline solution obtained from a filtrate in L-proline fermentation (50 ml, containing 20% of L-proline) was passed through the column at a flow rate of 25 ml/hr. The concentration of the pyrogen of the effluent was 0 ng/ml and Limulus test of the effluent was negative (−). Besides, the concentration of the pyrogen in the crude L-proline solution was 8.8 ng/ml and Limulus test thereof was positive (++).

EXAMPLE 15

The column used in Example 1 was washed in the same manner as described in Example 8. A solution of lysozyme chloride (0.5 g) in 0.005 M Tris hydrochloride buffer (100 ml, pH 9.0) containing about 10 ng/ml of pyrogen was passed through the column at a flow rate of SV=3. More than 90% of lysozyme was recovered in the effluent and the concentration of the pyrogen in the effluent was 0.1 ng/ml. When the effluent was subjected to Pyrogen test at a dose of 10 ml/kg, the body temperatures of the rabbits rose 0° C., 0.20° C. and 0.20° C., respectively and pyrogenicity of the effluent was deemed to be negative. Besides, when the lysozyme solution was directly subjected to Pyrogen test at a dose of 10 ml/kg (without subjecting to the treatment of the column), the body temperatures of the rabbits rose 1.00° C., 1.15° C. and 1.20° C., respectively and pyrogenicity of the solution was deemed to be positive.

EXAMPLE 16

The adsorbent obtained in Preparation 2 (ligand: histamine, carrier: aminohexylcellulose) was packed in a column (inner diameter: 20.8 mm, length: 27 mm) and a solution of crude urokinase (150 mg) in 0.01 M phosphate buffer (35 ml, pH 8.0) (Limulus test: ++)was passed through the column at a flow rate of SV=4. 64% of urokinase was recovered in the effluent and Limulus test of the effluent was negative (−).

EXAMPLE 17

The adsorbent obtained in Preparation 10 (ligand: 5-methylcytosine, carrier: carboxyhexylagarose) was packed in a column (inner diameter: 20.8 mm, length: 27 mm) and a solution of crystalline asparaginase (116 mg) in 0.05 M aqueous sodium chloride (20 ml) (Limulus test: ++) was passed through the column at a flow rate of SV=4. 94% of asparaginase was recovered in the effluent and Limulus test of the effluent was negative (−).

EXAMPLE 18

The column used in Example 1 was washed in the same manner as described in Example 8 and a solution of immunoglobulin G (50 mg) in 0.01 M phosphate buffer (50 ml, pH 7.5) (Limulus test: ++) was passed through the column at a flow rate of SV=3. 76% of immunoglobulin G was recovered in the effluent and Limulus test of the effluent was negative (−).

EXAMPLE 19

The column used in Example 1 was washed in the same manner as described in Example 8 and a solution of bovine insulin (100 mg) in 0.004 N hydrochloric acid (50 ml) containing 5 ng/ml of a pyrogen was passed through the column at a flow rate of SV=3. 85.6% of insulin was recovered in the effluent and the concentration of the pyrogen in the effluent was 0.4 ng/ml.

EXAMPLE 20

The adsorbent obtained in Preparation 14 (ligand: histamine, carrier: styrene-divinylbenzene copolymer, 8 ml) was packed in a column (inner diameter: 13 mm, length: 100 mm) and the column was washed in the same manner as described in Example 1. Then, pure water containing 4 ng/ml of a pyrogen (1 liter, Limulus test: ++) was passed through the column at a flow rate of 100 ml/hr. The concentration of the pyrogen in the effluent was 0.4 ng/ml and Limulus test of the effluent was negative (−).

EXAMPLE 21

The following operation was carried out by using the adsorbents obtained in Preparations 10 and 15 to 21.

Each adsorbent (8 ml) was washed with 1.5 M aqueous sodium chloride and packed in a sterilized column (inner diameter: 13 mm, length: 100 mm). The column was successively washed with 1.5 M aqueous sodium chloride (250 ml), pure (100 ml) and 0.05 M aqueous sodium chloride (100 ml), all of which being pyrogen free. A solution of a pyrogen in 0.05 M aqueous sodium chloride (400 ml, containing 1,000 ng of Escherichia coli 0128: B 12, LPS per 1 ml of the solution) was passed through the column at a flow rate of SV=12. The concentration of the pyrogen in the effluent was measured. The results are shown in Table 3.

TABLE 3

| No. | Adsorbents | Concentration of pyrogen (ng/ml effluent) |
|---|---|---|
| 1 | Adsorbent of Preparation 10 (ligand: 5-methylcytosine, carrier: carboxyhexylagarose) | 5.0 |
| 2 | Adsorbent of Preparation 15 (ligand: | |

TABLE 3-continued

| No. | Adsorbents | Concentration of pyrogen (ng/ml effluent) |
|---|---|---|
|  | histamine, carrier: aminoethyl-cellulose) | 4.6 |
| 3 | Adsorbent of Preparation 16 (ligand: histamine, carrier: aminobutyl-cellulose) | 0.46 |
| 4 | Adsorbent of Preparation 17 (ligand: histamine, carrier: aminoethyl-cellulose) | 0.06 |
| 5 | Adsorbent of Preparation 18 (ligand: histamine, carrier: aminobutyl-cellulose) | 0.24 |
| 6 | Adsorbent of Preparation 19 (ligand: histamine, carrier: aminohexyl-cellulose) | 0.05 |
| 7 | Adsorbent of Preparation 20 (ligand: histamine, carrier: aminooctyl-cellulose) | 0.18 |
| 8 | Adsorbent of Preparation 21 (ligand: histamine, carrier: aminodecyl-cellulose) | 1.6 |

EXAMPLE 22

The adsorbent obtained in Preparation 23 (ligand: histamine, carrier: styrene-divinylbenzene copolymer, 8 ml) was packed in a column (inner diameter: 13 mm, length: 100 mm) and the column was washed in the same manner as described in Example 1. When a solution of a pyrogne in 0.05 M aqueous sodium chloride (100 ml, containing 100 ng of *Escherichia coli* 0128: B 12, LPS per 1 ml of the solution) was passed through the column at a flow rate of SV=12, the concentration of the pyrogen in the effluent was 1.4 ng/ml.

EXAMPLE 23

The adsorbent obtained in Preparation 24 (ligand: histamine, carrier: styrene-divinylbenzene copolymer, 8 ml) was packed in a column (inner diameter: 13 mm, length: 100 mm) and washed in the same manner as described in Example 1. When a solution of a pyrogen in 0.05 M sodium chloride (100 ml, containing 100 ng of *Escherichia coli* 0128: B 12, LPS per 1 ml of the solution) was passed through the column at a flow rate of SV=12, the concentration of the pyrogen in the effluent was 1.8 ng/ml.

EXAMPLE 24

The adsorbent obtained in Preparation 25 (ligand: histamine, carrier: styrene-divinylbenzene copolymer, 8 ml) was packed in a column (inner diameter: 13 mm, length: 100 mm) and the column was washed in the same manner as described in Example 1. When a solution of a pyrogen in 0.05 M aqueous sodium chloride (100 ml, containing 100 ng of *Escherichia coli* 0128: B 12, LPS per 1 ml of the solution) was passed through the column at a flow rate of SV=12, the concentration of the pyrogen in the effluent was 1.3 ng/ml.

EXAMPLE 25

Each adsorbent obtained in Preparation 26 to 28 (8 ml) was packed in a column (inner diameter: 13 mm, length: 100 mm) and the column was washed in the same manner as described in Example 1. A solution of a pyrogen in 0.05 M aqueous sodium chloride (400 ml, containing 1,000 ng of *Escherichia coli* 0128: B 12, LPS per 1 ml of the solution) was passed through the column at a flow rate of SV=12. The concentration of the pyrogen in the effluent was measured. The results are shown in Table 4.

TABLE 4

| No. | Adsorbents | Concentration of pyrogen (ng/ml effluent) |
|---|---|---|
| 1 | Adsorbent of Preparation 26 (ligand: urocanic acid, carrier: aminohexyl-agarose) | 0.02 |
| 2 | Adsorbent of Preparation 27 (ligand: orotic acid, carrier: aminohexyl-agarose) | 0.15 |
| 3 | Adsorbent of Preparation 28 (ligand: uracil, carrier: aminohexylagarose) | 11 |

EXAMPLE 26

The adsorent obtained in Preparation 29 (ligand: histamine, carrier: styrene-divinylbenzene copolymer, 8 ml) was packed in a column (inner diameter: 13 mm, length: 100 mm) and the column was washed in the same manner as described in Example 1. When a solution of a pyrogen in 0.05 M aqueous sodium chloride (100 ml, containing 100 ng of *Escherichia coli* 0128: B 12, LPS per 1 ml of the solution) was passed through the column at a flow rate of SV=12, the concentration of the pyrogen in the effluent was 4.9 ng/ml.

EXAMPLE 27

Each adsorbent obtained in Preparation 31, 33 and 37 (8 ml) was packed in a column (inner diameter: 13 mm, length: 100 mm) and the column was washed by the same manner as described in Example 1. A solution of a pyrogen in 0.05 M aqueous sodium chloride (100 ml, containing 100 ng of *Escherichia coli* 0128: B 12, LPS per 1 ml of the solution) was passed through the column at a flow rate of SV=12. The concentration of the pyrogen in the effluent was measured. The results are shown in Table 5.

TABLE 5

| No. | Adsorbents | Concentration of pyrogen (ng/ml effluent) |
|---|---|---|
| 1 | Adsorbent of Preparation 31 (ligand: orotic acid, carrier: aminoethylated styrene-divinylbenzene copolymer) | 8.4 |
| 2 | Adsorbent of Preparation 33 (ligand: orotic acid, carrier: aminohexylated styrene-divinylbenzene copolymer) | 9.9 |
| 3 | Adsorbent of Preparation 37 (ligand: histamine, carrier: aminopropylated polyvinyl alcohol) | 7.6 |

What is claimed is:

1. A method for removing a pyrogen from a pyrogen-containing solution comprising contacting the solution with an adsorbent to adsorb the pyrogen, which is characterized in that the adsorbent comprises a water-insoluble carrier and a nitrogen-containing heterocyclic compound of the formula:

$$R-A-X \qquad (I)$$

wherein R is a nitrogen-containing heterocyclic group; A is single bond, alkylene or alkenylene; X is hydrogen or functional group; and the heterocyclic group and alkylene may be optionally substituted by one or more substituents, and the compound (I) being bonded to the carrier directly or through a spacer.

2. The method according to claim 1, wherein the nitrogen-containing heterocyclic compound is the compound (I) in which R is a nitrogen-containing heterocyclic group having an imidazole nucleus, pyrazole nucleus, pyrimidine nucleus, pyridazine nucleus, pyrazine nucleus, purine nucleus, acridine nucleus, triazole nucleus, oxadiazole nucleus, tetrazole nucleus, indazole nucleus, benzotriazole nucleus, benzopyridazine nucleus, benzopyrimidine nucleus, benzopyrazine nucleus or naphthyridine nucleus; A is single bond, an alkylene group having 1 to 12 carbon atoms or an alkenylene group having 2 to 12 carbon atoms; X is hydrogen, amino, hydroxy or carboxyl; and the nitrogen-containing heterocyclic group of R and the alkylene group of A may be optionally substituted with one or more substituents.

3. The method according to claim 1, wherein the nitrogen-containing heterocyclic compound is the compound (I) in which R is a nitrogen-containing heterocyclic group having an imidazole nucleus, pyrimidine nucleus, purine nucleus or acridine nucleus; A is single bond, ethylene or ethylene substituted with carboxyl; and X is hydrogen, amino, carboxyl or hydroxy.

4. The method according to claim 1, wherein the nitrogen-containing heterocyclic compound (I) is selected from histidine, histamine, urocanic acid, uracil, orotic acid, cytosine, 5-methylcytosine, 2-amino-4,6-dimethylpyrimidine, 2-amino-4-hydroxy-6-methylpyrimidine, adenine and 6,9-diamino-2-ethoxyacridine.

5. The method according to claim 1, wherein the nitrogen-containing heterocyclic compound (I) is histidine, histamine or urocanic acid.

6. The method according to claim 1, 2, 3, 4 or 5, wherein the water-insoluble carrier is a water-insoluble carrier having hydroxy group, amino group, carboxyl group or a halogen atom in the molecule thereof.

7. The method according to claim 6, wherein the adsorbent is the nitrogen-containing heterocyclic compound (I) bonded to the water-insoluble carrier directly or through a spacer by a diazo linkage or an acid-amide linkage or by means of at least one of cyanogen halide, a monoepoxide, a bisepoxide, a halogenoacetyl halide, cyanuric halide and an aliphatic dialdehyde.

8. The method according to claim 7, wherein the spacer is selected from the group consisting of $NH_2(CH_2)_nNH_2$, $NH_2(CH_2)_nCOOH$, $NH_2(CH_2)_nOH$ and $HOOC(CH_2)_nCOOH$, wherein n is an integer of 1 to 12.

9. The method according to claim 6, wherein the adsorbent is the nitrogen-containing heterocyclic compound (I) bonded to the water-insoluble carrier directly or through a spacer by a diazo linkage or an acid-amide linkage or by means of at least one of cyanogen bromide, epichlorohydrin, cyanuric chloride and glutaraldehyde.

10. The method according to claim 9, wherein the spacer is selected from the group consisting of $NH_2(CH_2)_nNH_2$, $NH_2(CH_2)_nCOOH$, $NH_2(CH_2)_nOH$ and $HOOC(CH_2)_nCOOH$, wherein n is an integer of 1 to 12.

11. The method according to claim 1, 2, 3, 4 or 5, wherein the water-insoluble carrier is selected from the group consisting of a polysaccharide, a hydroxyalkylpolystyrene resin, a polyvinylalcohol, an aminoalkylpolysaccharide, a p-aminobenzylpolysaccharide, chitosan, an aminoalkylpolystyrene resin, a polyacrylamide, an aminoalkylpolyacrylamide, an aminoalkyl-porous glass, a carboxyalkylpolysaccharide, a carboxyalkylpolyacrylamide, a carboxylic acid resin and a halogenoalkyl-polystyrene resin.

12. The method according to claim 1, 2, 3, 4 or 5, wherein the water-insoluble carrier is a polysaccharide having hydroxy group, amino group or carboxyl group in the molecule thereof.

13. The method according to claim 1, 2, 3, 4 or 5, wherein the water-insoluble carrier is selected from the group consisting of a polysaccharide, an aminoalkylpolysaccharide and a carboxyalkylpolysaccharide.

14. The method according to claim 1, 2, 3, 4 or 5, wherein the water-insoluble carrier is selected from the group consisting of cellulose, agarose, aminoalkylcellulose, aminoalkylagarose, carboxyalkylcellulose and carboxyalkylagarose.

15. The method according to claim 1, wherein the removal of a pyrogen is carried out by passing a pyrogen-containing solution through a column packed with the adsorbent to adsorb pyrogen on the adsorbent.

* * * * *